(12) United States Patent
Strohmaier et al.

(10) Patent No.: US 7,922,884 B2
(45) Date of Patent: Apr. 12, 2011

(54) DEVICE FOR MEASURING THE PRESSURE IN A GAS MIXTURE

(75) Inventors: Rainer Strohmaier, Stuttgart (DE); Martin Bauer, Karlsruhe (DE); Bernhard Kamp, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 1377 days.

(21) Appl. No.: 10/578,339

(22) PCT Filed: Nov. 8, 2004

(86) PCT No.: PCT/EP2004/052865
§ 371 (c)(1), (2), (4) Date: May 5, 2006

(87) PCT Pub. No.: WO2005/047841
PCT Pub. Date: May 26, 2005

(65) Prior Publication Data
US 2007/0144904 A1    Jun. 28, 2007

(30) Foreign Application Priority Data
Nov. 12, 2003  (DE) .................................. 103 52 797

(51) Int. Cl.
*G01N 27/41* (2006.01)
(52) U.S. Cl. .......................... 204/424; 204/421; 73/23.29
(58) Field of Classification Search .................. 204/410, 204/411, 421–429; 205/781, 783.5–785, 205/787; 72/23.31, 23.32
See application file for complete search history.

(56) References Cited

U.S. PATENT DOCUMENTS

| 3,658,479 | A | | 4/1972 | Heijne et al. | |
|---|---|---|---|---|---|
| 5,021,137 | A | * | 6/1991 | Joshi et al. | 204/242 |
| 5,948,963 | A | * | 9/1999 | Kato et al. | 73/23.2 |
| 6,338,782 | B1 | * | 1/2002 | Imamura et al. | 204/424 |
| 6,495,027 | B1 | * | 12/2002 | Stahl et al. | 205/781 |
| 7,048,844 | B2 | * | 5/2006 | Chen et al. | 205/789.5 |
| 2002/0175077 | A1 | * | 11/2002 | Wahl et al. | 204/424 |

FOREIGN PATENT DOCUMENTS

| DE | 31 22 861 | 12/1982 |
|---|---|---|
| DE | 196 21 433 | 12/1996 |
| EP | 0 408 030 | 1/1991 |
| EP | 1 139 096 | 10/2001 |

* cited by examiner

*Primary Examiner* — Ula C Ruddock
*Assistant Examiner* — Gurpreet Kaur
(74) *Attorney, Agent, or Firm* — Kenyon & Kenyon LLP (57) ABSTRACT

A device for measuring the pressure of a gas mixture composed of gas components has an amperometric sensor that works on the limiting current principle, having two electrodes connected to a direct voltage that are situated on a solid electrolyte, of which one electrode is covered by a diffusion barrier, and a measuring element for measuring the limiting current flowing via electrodes as a measure for the gas pressure. For the purpose of error-free measurement of the gas pressure in a gas mixture in which the concentration of the gas components fluctuates with time, means are provided which fix the mole fraction of a gas component, drawn upon for pressure measurement, that is present upstream of the diffusion barrier at a constant 100%, at least during the pressure measuring phase. In one preferred exemplary embodiment, these means include a storage volume that is adjacent to the diffusion barrier which is separated from the gas mixture by a diffusion path, and two electrodes, situated on the solid electrolyte, for pumping of the gas component into the storage volume.

20 Claims, 4 Drawing Sheets

DEVICE FOR MEASURING THE PRESSURE IN A GAS MIXTURE

FIELD OF THE INVENTION

The present invention relates to a device for measuring the pressure in a gas mixture.

BACKGROUND INFORMATION

German Patent No. 31 22 861 describes a device for measuring the absolute pressure of air. This device has an amperometric sensor that work on the limiting diffusion current principle, called a polarographic measuring cell there, which is made up of an oxygen ion-conducting solid electrolyte element and two electrodes situated on opposite sides of the solid electrolyte element, of which the electrode operated as a cathode is exposed to the air that is to be measured via a porous diffusion layer that covers the electrode. A constant direct voltage is applied to the electrodes. As a result of the electrochemical reduction of the oxygen, the latter is used up at the cathode. The concentration gradient of the oxygen thus created, brings about a diffusion current of oxygen through the diffusion layer. The concentration gradient is the controlling factor for the reduced oxygen quantity, and thus for the measuring signal. The pores in the diffusion layer preferably have a diameter that is small compared to the mean free path of the oxygen molecules. The transport of the oxygen ions, under these conditions, takes place above all by the so-called Knudsen diffusion, in which a strong pressure dependency of the diffusion current, and thus of the measuring signal, comes about. The device is also equipped with controlled heating, which heats the sensor or the measuring cell to a constant temperature above about 600° C.

SUMMARY

A device for measuring gas pressure according to an example embodiment of the present invention, may have the advantage that it measures very accurately the pressure in a gas mixture in which the concentration or the mole fraction of gas components is not constant, as is the mole fraction of oxygen in the air, but fluctuates as a function of time, and it does this by holding the mole fraction of a gas component, which is being drawn upon for the pressure measurement, to 100% constant, upstream of the diffusion barrier, at least during the measuring phase, thus at the diffusion barrier there is present the pure gas component drawn upon for the pressure measurement. The measured value of the amperometric sensor is determined by the mass flow J of the gas component that diffuses through the diffusion barrier. In the case of the Knudsen diffusion, since the mass flow J is equal to the product of the diffusion coefficient D of the diffusion barrier and the partial pressure of the gas component being drawn upon P(GK), and this, in turn, is equal to the product of the total pressure P of the gas mixture, the mole fraction of the gas component x(GK) and the diffusion coefficient D of the diffusion barrier, and thus $$J \approx D \cdot P(GK) = D \cdot x(GK) \cdot P$$

applies, because the mole fraction x(GK) upstream of the diffusion barrier is held to 100% constant, and diffusion coefficient D, at a suitable design of the diffusion barrier, is independent of total pressure P, the total pressure is proportional to the mass flow, and thus also to the measured value of the amperometric sensor. The gas component drawn upon for the pressure measurement is preferably a gas component contained in the gas mixture, but it may also be a gas component that first forms at the amperometric sensor, for instance, by the splitting off of oxygen ions of water components contained in rich exhaust gas. The example device according to the present invention may be suitable for high temperatures and suitable for use in measuring the gas pressure in hot exhaust gases of internal combustion engines.

According to one preferred specific embodiment of the present invention, the means for fixing the 100% mole fraction of the gas component include a storage volume for the gas component, that is connected upstream of the diffusion barrier, in the solid electrolyte, that is shut off from the gas mixture by a diffusion path, and include two electrodes mounted on the solid electrolyte which, when a corresponding constant voltage is applied, pump molecules of the gas component all the way through the solid electrolyte into the storage volume, so that the storage volume is filled exclusively with the pure gas component. If oxygen is drawn upon as the gas component for pressure measurement, and the outer electrode exposed to the gas mixture, such as the exhaust gas of an internal combustion engine, is operated as an anode, then at the three-phase boundary of solid electrolyte, electrode and gas mixture a reduction takes place of the oxygen to oxygen ions, which are conducted through the solid electrolyte and are oxidized back to elemental oxygen at the anode.

According to one advantageous specific embodiment of the present invention, the diffusion barrier has a porosity that is required for a so-called Knudsen diffusion. Such a Knudsen diffusion is achieved if the diameter of the pores of the diffusion barrier is small compared to the mean free path of the gas component molecules, for instance, of the oxygen molecules. As was described above, the diffusion coefficient of the diffusion barrier is then independent of the total pressure of the measured gas.

According to one advantageous specific embodiment of the present invention, the diffusion path is laid out in such a way that it has a low pressure gradient, that is, a very low pressure drop over the diffusion path. The diffusion path is thus permeable enough to make possible a pressure adjustment between the storage volume and the gas mixture, and nevertheless prevents the gas mixture from getting into the storage volume.

The storage volume and the diffusion path may be implemented in different ways, according to additional specific embodiments of the present invention. Preferably, the storage volume is created by a chamber formed in the solid electrolyte which borders directly on the diffusion barrier. The diffusion path is formed by a second porous diffusion barrier made of ceramic material, such as aluminum oxide ($Al_2O_3$), which delimits the chamber from the exhaust gas. The second diffusion barrier can be subdivided into partial barriers, in this context, between which there is a cavity in each case. The diffusion path may also be formed by at least one extended channel. Likewise it is possible to design the diffusion path and the storage volume as a unit, to be made of a porous ceramic.

According to one advantageous specific embodiment of the present invention, the electrodes for pumping the gas components are additional electrodes, of which one is situated as an additional electrode operated as a cathode within the storage volume, for instance, in the chamber, and the other additional electrode operated as an anode is exposed to the gas mixture, and a direct voltage is applied to the additional electrodes. This has the advantage that the pressure measurement is able to be carried out continuously, that is, without interruption. In this context, one electrode can advantageously be saved, by putting together the additional electrode operated as an anode with the electrode of the amperometric sensor that is not blocked off shielded by the diffusion barrier.

According to an alternative specific embodiment of the present invention, the electrodes of the amperometric sensor are drawn upon as electrodes for the pumping of the gas component, and for this purpose, before the actual pressure measuring phase, the electrode voltage is reversed in polarity in such a way that the electrode facing the diffusion barrier operates as an anode. This has the advantage that one may do without additional electrodes and their corresponding supply leads. There is a certain disadvantage in that the pressure measurement can only be carried out discontinuously in those phases in which the electrode, of the amperometric sensor, facing the diffusion barrier is being operated as a cathode.

According to one advantageous specific embodiment of the present invention, the exhaust gas of an internal combustion engine in motor vehicles is used as the gas mixture, and oxygen is used as the gas component drawn upon for the pressure measurement. This application of the device for exhaust gas pressure measurement yields a series of advantageous application possibilities in the vehicle. In this way, the measuring accuracy of lambda probes used, which is a function of the pressure, may be improved by compensation of the pressure dependency. Furthermore, by the exhaust gas pressure measurement, the control of the exhaust gas recirculation may be improved, in the boost-pressure control the exhaust gas counterpressure may be limited, the monitoring of a Diesel particulate filter may be improved and the detection of the degree of saturation of Diesel particulate filters may be improved by measuring the absolute pressure, since knowledge of the absolute pressure of the exhaust gas makes possible a more exact determination of the flow resistance of the Diesel particulate filter.

The example device according to the present invention for gas pressure measurement is especially, advantageously applicable in a sensing element for determining the oxygen content of the exhaust gas of internal combustion engines, so-called lambda probes, especially broadband lambda probes. In this connection, there is the problem that the probe signal is a function of the exhaust gas pressure, and the measuring error caused by this has to be compensated for. The example device according to the present invention is particularly easily integrated into such sensing elements, since a major part of the component parts of the sensing element is able to be used for the functionality of the device for the gas pressure measurement, and, this being the case, only a slight additional expenditure is required for the gas pressure measurement. In this context, both a continuous operation of the pressure measurement device is possible, so that during a running lambda measurement the gas pressure may also be continuously measured and the lambda measurement may be continuously corrected, and a discontinuous operation is also possible, in which the gas pressure measurement is carried out only at intervals, that is, in response to temporarily interrupted lambda measurement. Whereas in the last case, besides the formation of the oxygen storage volume and the diffusion path in the solid electrolyte, no additional component parts and supply lead are required for the pressure measurement, in the first case, additionally, one electrode and one supply lead to this electrode are required.

According to alternative specific embodiments of the discontinuous operation, either the reference electrode and the outer pump electrode or the internal and external pump electrode is drawn upon for pumping oxygen into the reference channel, in the first case, and in the second case into the storage volumes, developed at the measuring chamber, and enclosed by diffusion barrier and diffusion path, for which an appropriate voltage is applied to the electrodes discussed. Thereafter, the polarity of the voltage is reversed, and the limiting current that flows between the electrodes of the pump cell is measured. In the time interval of the pressure measurement, the lambda measurement of the sensing element is interrupted.

Example embodiments of the present invention include sensing elements, preferably broadband lambda probes, having an integrated device for gas pressure measurement. Such sensing elements have the advantage that, besides the exact measurement of the lambda value, the additional advantages, explained above, because of the integrated measuring device, can still be used, with reference to the boost-pressure control and the Diesel particulate filter monitoring, without having to install separate pressure sensors.

BRIEF DESCRIPTION OF THE DRAWINGS

The present invention is described in further detail below in terms of exemplary embodiments shown in the figures.

DETAILED DESCRIPTION OF EXAMPLE EMBODIMENTS

Figure 1:
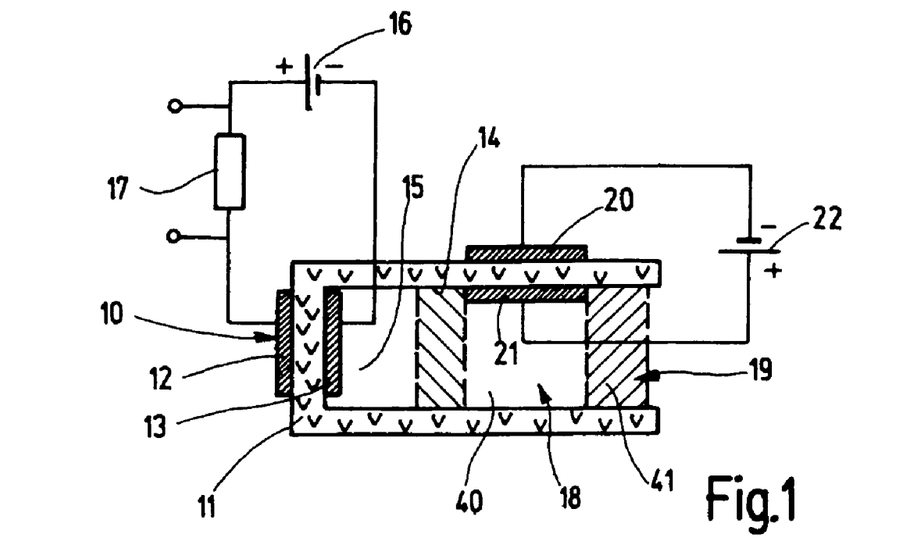
FIG. 1 shows a cross section of a device for gas pressure measurement having continuous pressure measurement.

The device for measuring the pressure in a gas mixture, shown in schematic form in FIG. 1, has an amperometric sensor 10 that operates according to the limiting current principle. This sensor 10 measures the concentration of a gas component, for instance, the oxygen concentration in the exhaust gas of an internal combustion engine. Amperometric sensor 10 has a solid electrolyte 11 and two electrodes 12, 13 mounted on the solid electrolyte 11, as well as a porous diffusion barrier 14, in which the diameters of the pores are small compared to the mean free path of the gas component whose concentration is being measured. Because of this porosity, a so-called Knudsen diffusion takes place in diffusion barrier 14, whereby the diffusion coefficient of diffusion barrier 14 becomes independent of the total pressure of the gas mixture. Of the two electrodes 12, 13, a first one is situated outside on solid electrolyte 11, whereas the second is situated in a cavity 15 that is developed in solid electrolyte 11, which is enclosed by diffusion barrier 14. In this context, diffusion barrier 14 may also be mounted directly on electrode 13, so that cavity 15 drops out. A constant direct voltage is applied to the two electrodes 12, 13 and this is done in such a manner that outer first electrode 12 is operated as an anode, and second electrode 13 positioned in cavity 15 is operated as a cathode. Into the circuit of the two electrodes 12, 13 that are connected to voltage source 16, a measuring resistor 17 is inserted from which a voltage proportional to the limiting current flowing in the circuit can be picked off. To simplify the description, in the following, the manner of operating of amperometric sensor 10 for measuring the oxygen concentration in the exhaust gas of an internal combustion engine is described, the concentration of any gas component, for instance, even hydrogen, in any gas mixture being able to be recorded.

When a direct voltage is applied to electrodes 12, 13, the measuring signal of amperometric sensor 10 that is able to be picked off at measuring resistor 17 is determined by mass flow J of the oxygen that passes through diffusion barrier 14. This mass flow is calculated as $$J = D \cdot P(O_2) = D \cdot x(O_2) \cdot P,$$

D being the diffusion coefficient of diffusion barrier 14, $P(O_2)$ the partial pressure of the oxygen, P the total pressure of the exhaust gas and $X(O_2)$ the mole fraction of the oxygen. Since Knudsen diffusion takes place in diffusion barrier 14 because of the selected pore size, diffusion coefficient D is independent of total pressure P, and the measuring signal is proportional to the partial pressure of the oxygen $P(O_2)$. In the sensor described, the mole fraction of the oxygen $x(O_2)$ in front of diffusion barrier 14 is fixed at 100%, so that pure oxygen is present in front of diffusion barrier 14. That being the case, mass flow J is directly proportional to total pressure P of the exhaust gas, and the limiting current flowing over measuring resistor 17 is a measure for total pressure P of the exhaust gas. The fixing of the mole fraction of the oxygen $x(O_2)$ at 100% is performed by providing a storage volume 18 for oxygen that is directly adjacent to diffusion barrier 14 in solid electrolyte 11, which is connected to the exhaust gas via a diffusion path 19, and additional measures are taken to pump oxygen all the way through solid electrolyte 11 into storage volume 18, so that in storage volume 18, the mole fraction of the oxygen $x(O_2)$ is held to 100%, at least during the pressure measurement phase of the device, that is, storage volume 18 is filled with pure oxygen. Diffusion path 19 is designed so that it has a low pressure gradient, and because of this, a pressure adjustment is possible between storage volume 18 and the exhaust gas, and that it prevents diffusion of the exhaust gas into reservoir 18.

Figure 2:
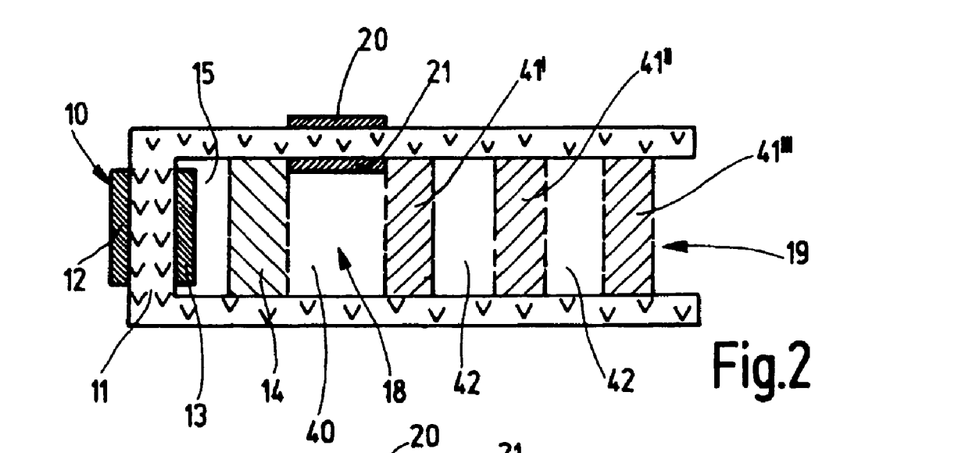
FIG. 2-4 shows in each case, the same representation as in FIG. 1, of a modified device for gas pressure measurement according to three exemplary embodiments.
Figure 3:
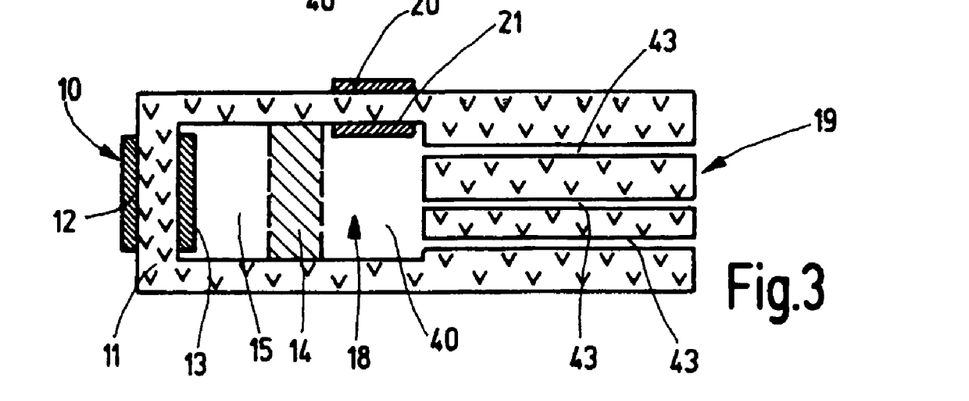

In the exemplary embodiment of FIG. 1, storage volume 18 is made available by a chamber 40 developed between diffusion barrier 14 and diffusion path 19 in the solid electrolyte, and diffusion path 19 is formed by a porous diffusion barrier 41 made of ceramic material, such as aluminum oxide ($Al_2O_3$). Instead of the one diffusion barrier 41, several diffusion barriers 41', 41" may be situated one after the other, a cavity 42 being present in each case between the individual diffusion barriers (FIG. 2). Diffusion path 19 may also be implemented by one or more elongated channels 43, which, by appropriate design of their cross section and their length are sufficient for the requirements of diffusion path 19 (FIG. 3). Storage volume 18 and diffusion path 19 may be developed as a unit, for example, as a filler piece 44 made of ceramic material, such as aluminum oxide ($Al_2O_3$), which is directly adjacent to diffusion barrier 14 (FIG. 4).

In order to pump oxygen into storage volume 18 or chamber 40, two additional electrodes 20, 21 are mounted on solid electrolyte 11, in the exemplary embodiment according to FIG. 1, in such a way that the one additional electrode 20 is exposed to the exhaust gas and the other additional electrode 21 is situated in chamber 40. Using a voltage source 22, a constant direct voltage is applied to the two additional electrodes 20, 21 in such a way that additional electrode 21 that is situated in chamber 40 functions as an anode and additional electrode 20 that is exposed to the exhaust gas functions as a cathode. At the three-phase boundary of solid electrolyte 11, additional electrode 20 and exhaust gas, there takes place a reduction of oxygen to oxygen ions, which is passed through solid electrolyte 11 and is oxidized back again to elemental oxygen at additional electrode 21. In this manner, oxygen is constantly being pumped into chamber 40. Second diffusion barrier 41 which forms diffusion path 19 is designed in such a way that it has a low pressure gradient, that is, a low pressure decline or pressure loss over the diffusion path. Because of this design of second diffusion barrier 41, the latter is permeable enough to produce, on the one hand, a pressure compensation between chamber 40 and the exhaust gas, and, on the other hand, to prevent diffusion of the exhaust gas into chamber 40. The oxygen diffuses all the way through first diffusion barrier 14 and reaches electrode 13 of amperometric sensor 10. At the three-phase boundary of solid electrolyte 11, electrode 13 and oxygen, the oxygen is again reduced to oxygen ions, which wander all the way through solid electrolyte 11, and are oxidized back to oxygen again at first electrode 12 of amperometric sensor 10. First diffusion barrier 14 is responsible for converting each arriving oxygen molecule directly to oxygen ions, so that in cavity 15 an oxygen concentration near zero always prevails. The oxygen ion transport through solid electrolyte 11, the so-called mass flow J, brings about a limiting current flowing through measuring resistor 17 which, according to the above comments, is a measure of the total exhaust gas pressure.

Figure 4:
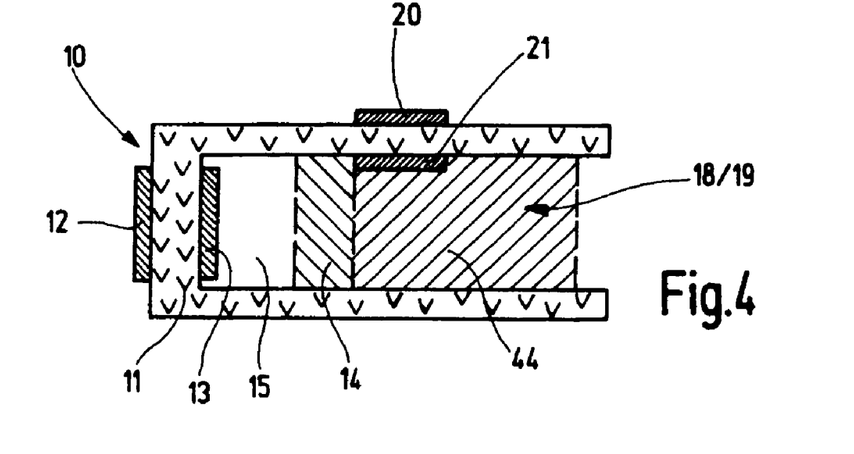

In the exemplary embodiment shown in FIGS. 2-4, the positioning of electrodes 12, 13 and additional electrodes 20, 21 is undertaken in the same way as in FIG. 1. Additional electrode 21, in this context, is always situated in storage volume 18, which is a chamber bordered by diffusion barrier 14 and diffusion path 19 in the exemplary embodiments of FIGS. 2 and 3. In the exemplary embodiment of FIG. 4, the "chamber" is filled in by the porous ceramic material of diffusion path 19 developed as diffusion barrier 41. The ceramic material, for instance, aluminum ($Al_2O_3$) covers additional electrode 21 and extends all the way to diffusion barrier 41.

Figure 5:
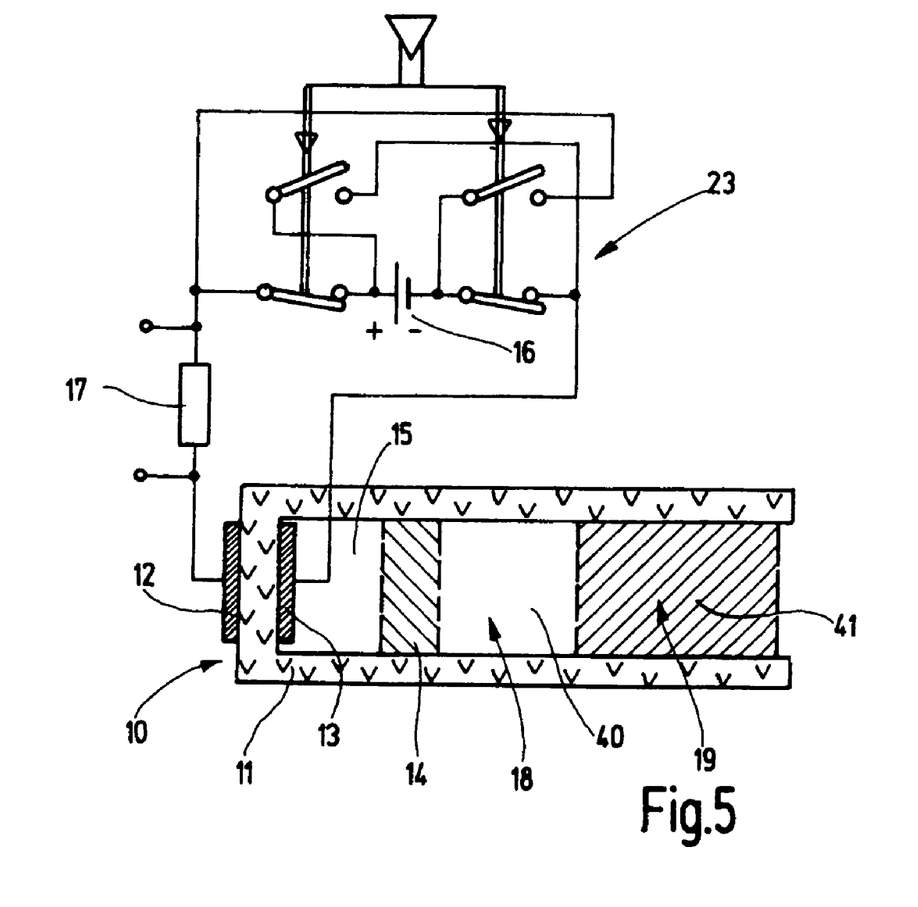
FIG. 5 shows a cross section of a device for gas pressure measurement having discontinuous pressure measurement.

The exemplary embodiment of the device for the measurement of gas pressure, shown in FIG. 5, is modified to the extent that the additional electrodes having a voltage source have been eliminated, and, for pumping oxygen into storage volume that is again made available by a chamber 40, electrodes 12, 13 of amperometric sensor 10 are used, and the latter has to be switched over at intervals from a measuring phase, in which the gas pressure is measured, to a pumping phase, in which chamber 40 is filled with pure oxygen. For this purpose, a switching device 23, shown schematically, is provided, by whose switchover the two electrodes 12, 13 of amperometric sensor 10 are able to be operated alternately as an anode or as a cathode. For the pumping of oxygen, switching device 23 is switched in such a way that second electrode 13 is operated as an anode and first electrode 12 is operated as a cathode, so that pure oxygen is pumped into cavity 15 and all the way through diffusion barrier 14 into chamber 40, as described above. For pressure measurement, switching device 23 is now switched back from the switching position shown in FIG. 5, so that first electrode 12 is operated as an anode and second electrode 13 is operated as a cathode. Because of this, as was described in connection with FIG. 1, oxygen ions wander from electrode 13 all the way through solid electrolyte 11 to first electrode 12, and the limiting current setting in thereby, in the circuit of electrodes 12, 13, is a measure of the total pressure of the exhaust gas. The advantage of this device is that additional electrodes 20, 21 including supply leads may be saved. In this case, only a discontinuous operation is possible in which alternately oxygen is pumped and the exhaust gas pressure is measured. Naturally, the design of storage volume 18 and diffusion path 19 in the exemplary embodiment of FIG. 5 may be undertaken as shown in FIGS. 2, 3 and 4.

The device for gas pressure measurement described above in various exemplary embodiments is particularly suitable for use in internal combustion engines of motor vehicles, since it is integrated especially easily into the lambda probes used there for exhaust gas measurement, and may offer the following advantages:

The lambda signal, which is a measure for the concentration of oxygen in exhaust gas, is a function of gas pressure, and consequently is prone to error. Using the gas pressure device, the exhaust gas pressure is able to be measured, and the error compensated for. In internal combustion engines having exhaust gas recirculation, the control of the exhaust gas recirculation may be improved by knowing the exhaust gas pressure. Likewise, in boost-pressure control, the exhaust gas counterpressure is able to be limited. In Diesel engines having Diesel particulate filters, the monitoring of the Diesel particulate filters may be monitored because of the measurement of the exhaust gas pressure. In this context, the detection of the degree of saturation may be greatly improved by supplementing the pressure difference signal measured by the usual pressure sensors with an absolute pressure signal measured using the gas pressure measuring device, since the flow resistance of the Diesel particulate filter may be determined more accurately.

Figure 6:
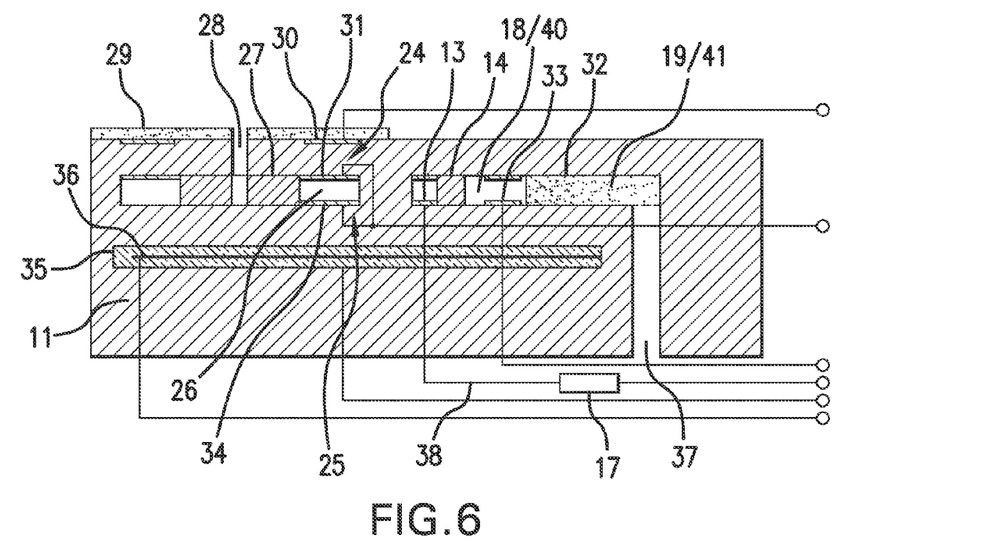
FIG. 6 shows a longitudinal section of a broadband lambda probe having an integrated pressure measurement device for continuous pressure measurement.
Figure 7:
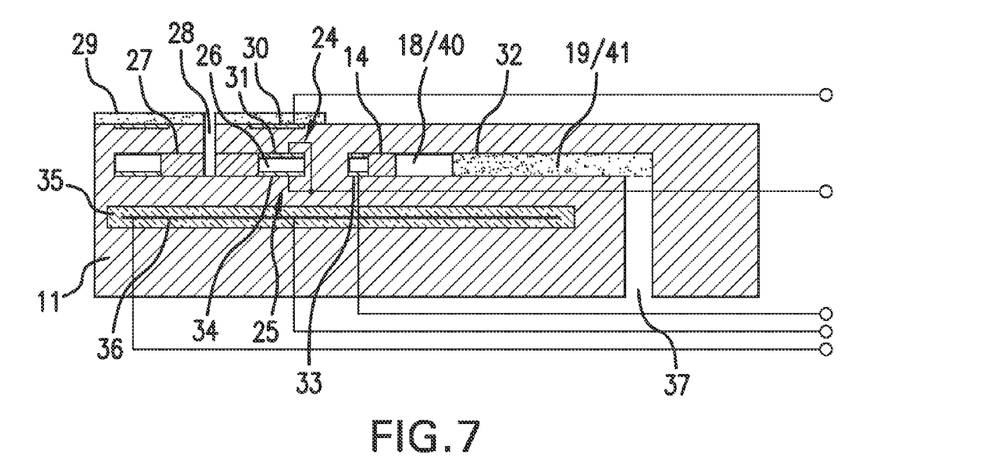
FIG. 7 shows a longitudinal section of a broadband lambda probe having an integrated pressure measurement device for discontinuous pressure measurement.
Figure 8:
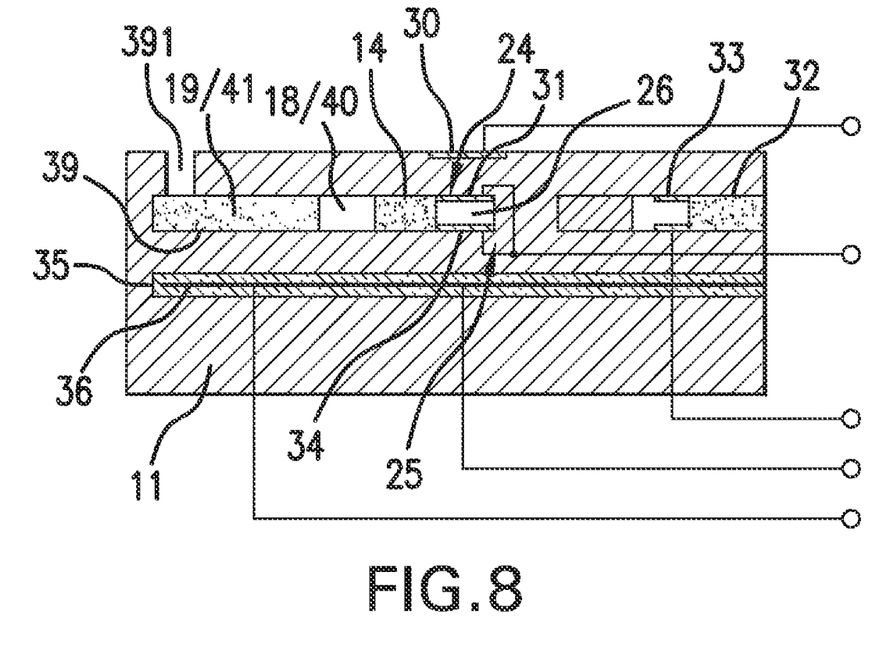
FIG. 8 shows a longitudinal section of a broadband lambda probe having an integrated pressure measurement device for discontinuous pressure measurement.

FIGS. 6-8 show schematically three exemplary embodiments of a so-called broadband lambda probe having an integrated pressure measurement device. Since the lambda probe itself represents an amperometric sensor 10, it may be drawn upon by minor modifications to measure the pressure of the exhaust gas at the same time.

As is conventional, amperometric sensor 10 has a solid electrolyte 11 produced as a layer composite made of yttrium-stabilized zirconium oxide ($ZrO_2$), using which a so-called pump cell 24 and a concentration cell or Nernst cell 25 is constructed. For the construction of pump cell 24, a measuring chamber 26 is provided, in solid electrolyte 11, which is separated from an exhaust gas access hole 28 by a diffusion barrier 27. On the surface of solid electrolyte 11 there is an outer pump electrode 30 that is covered by a porous protective layer 29, and in the interior of measuring chamber 26 on solid electrolyte 11 there is situated an internal pump electrode 31 of pump cell 24. For the design of Nernst cell 25, in solid electrolyte 11 a reference gas channel 32 is provided, in which a reference electrode of Nernst cell 25 is exposed to a pumped oxygen reference. A Nernst or measuring electrode 34 of Nernst cell 25 is situated in measuring chamber 26 on solid electrolyte 11. In addition, in solid electrolyte 11 there is also present a heating device having an electrical heat conductor 36 that is embedded in an insulation 35, such as aluminum oxide ($Al_2O_3$). The way of functioning of the broadband lambda probe is described, for example, in German Patent Application No. DE 199 41 051 A1.

In the exemplary embodiment in FIG. 6, the continuously measuring gas pressure measurement device shown in FIG. 1 is integrated in that reference gas channel 32 is provided with an opening 37 charged with exhaust gas, and in reference gas channel 32, between this opening 37 and reference electrode 33, diffusion path 19 and storage volume 18, that is arranged upstream of it in the direction of reference electrode 33, are developed for oxygen. Storage volume 18 is in turn made available by a chamber 40, and diffusion path 19 is designed as porous diffusion barrier 41 having a small pressure gradient. In reference gas channel 32, on the side of reference electrode 33 facing away from diffusion path 19, electrode 13 is situated on solid electrolyte 11, and it is used together with outer pump electrode 30 for measuring pressure, so that in comparison to FIG. 1, outer pump electrode 30 of pump cell 24 fills the same function as electrode 12 of amperometric sensor 10. Measuring resistor 17 is situated in supply lead 38 to electrode 13. Electrode 13 is separated by diffusion barrier 14 from chamber 40 that accommodates reference electrode 33. Together with outer pump electrode 30 of pump cell 24, reference electrode 33 implements the oxygen pumping into chamber 40, so that there is always 100% oxygen present in the latter.

The gas pressure measuring device working with discontinuous pressure measurement, according to FIG. 5, is integrated in each case in the lambda probes shown in FIGS. 7 and 8. In both exemplary embodiments the actual lambda probe for exhaust gas measurement is designed the same as that in FIG. 6, so that equal component parts are provided with the same reference numerals.

In the exemplary embodiment of FIG. 7, just as in exemplary embodiment of FIG. 6, reference gas channel 32 is provided with an opening 37, which is charged with exhaust gas. Between opening 37 and reference electrode 33, in reference gas channel 32, diffusion path 19 (diffusion barrier 41) and storage volume 18 (chamber 40) arranged in front of it is formed. Storage volume 18 (chamber 40) is separated from reference electrode 33 by diffusion barrier 14 having the Knudsen diffusion. As described above in connection with FIG. 5, the oxygen pumping all the way into chamber 40 takes place here by the corresponding wiring of outer pump electrode 30 of pump cell 24 and of reference electrode 33, so that, compared to FIG. 5, outer pump electrode 30 of pump cell 24 and reference electrode 33 fills the function of electrodes 12, 13 of amoerometric sensor 10. For the measurement of the exhaust gas pressure, as described for FIG. 5, the voltage potentials at outer pump electrode 30 and reference electrode 33 are switched over.

In the exemplary embodiment of the lambda probe having an integrated pressure measuring device of FIG. 8, pump cell 24 is drawn upon at intervals for measuring gas pressure. In order to do this, in solid electrolyte 11, a connecting channel 39, having a channel opening 391 towards the exhaust gas, is produced to measuring chamber 26, in which diffusion path 19 and storage volume 18 arranged in front of it, in the direction of measuring chamber 26, are developed for oxygen. Diffusion path 19 is designed as a porous diffusion barrier 41, made of ceramic material, and storage volume 18 is designed as chamber 40. Knudsen diffusion takes place in first diffusion barrier 14. Second diffusion barrier 41, once again, has a pressure gradient that is as low as possible, so that a pressure adjustment between chamber 40 and the exhaust gas can take place. As in the lambda probe according to FIG. 7, here too the gas pressure measurement takes place in short-time intervals in which the lambda measurement is interrupted. The gas pressure measurement takes place as described in connection with FIG. 5, the two pump electrodes 30, 31 of pump cell 24 taking over the function of electrodes 12 and 13 in FIG. 5, and, during the gas pressure measurement, a switchover is undertaken of the voltage applied at electrodes 30, 31 from the pumping phase to the measuring phase.

What is claimed is:

1. A device for measuring pressure in a gas mixture, comprising:
    an amperometric sensor that operates according to a limiting current principle, the sensor including two first electrodes mounted on a solid electrolyte, a direct voltage being applied to the first electrodes, wherein one of the first electrodes is shielded by a diffusion barrier;

a measuring element configured to measure the limiting current flowing via the first electrodes as a measure of the gas pressure; and an arrangement configured to fix, at least during a pressure measuring phase, a mole fraction of a gas component drawn upon for the pressure measurement upstream of the diffusion barrier to a constant 100%, wherein the arrangement includes a storage volume for the gas component, the storage volume be arranged in front of the diffusion barrier in the solid electrolyte, a diffusion path closing off the storage volume in a direction of the gas mixture, the arrangement further including two second electrodes situated at the solid electrolyte to pump the gas component all the way through the solid electrolyte into the storage volume, wherein the sensor includes a Nernst cell made up of a solid electrolyte and two second electrodes situated thereon, a first one of the second electrodes being a measuring electrode and being situated in a measuring chamber developed in the solid electrolyte, and a second one of the second electrodes being a reference electrode and being exposed to a pumped oxygen reference in a reference gas channel developed in the solid electrolyte; and a pump cell made up of a solid electrolyte and two pump electrodes situated thereon, an outer one of the pump electrodes situated thereon, an outer one of the pump electrodes being exposed to the exhaust gas and an inner one of the pump electrodes being situated in the measuring chamber;

wherein the reference gas channel is provided with an opening that is exposed to the exhaust gas, and wherein in the reference gas channel between the reference electrode and the opening, the diffusion path and the storage volume are developed, and an outer one of the pump electrodes and the reference electrode being used as intervals for pumping oxygen and for measuring gas pressure by switching over their voltage potentials.

2. The device as recited in claim 1, wherein the diffusion path has a small pressure gradient.

3. The device as recited in claim 1, wherein the storage volume is formed by a chamber adjacent to the diffusion barrier, and the diffusion path is formed by a second diffusion barrier made of a ceramic material that closes off the chamber.

4. The device as recited in claim 3, wherein the ceramic material is aluminum oxide ($Al_2O_3$).

5. The device as recited in claim 1, wherein the storage volume is formed by a chamber that is adjacent to the diffusion barrier, and the diffusion path is formed by at least one extended channel.

6. The device as recited in claim 1, wherein the storage volume and the diffusion path are formed by a porous filler piece made of a ceramic material which borders on the diffusion barrier.

7. The device as recited in claim 6, wherein the ceramic material is aluminum oxide ($Al_2O_3$).

8. The device as recited in claim 1, wherein the diffusion barrier has a porosity that is required for Knudsen diffusion.

9. The device as recited in claim 1, wherein the second electrodes for pumping the gas component are additional electrodes, one of the additional electrodes, operated as an anode, being situated within the storage volume and one of the additional electrodes, operated as a cathode, being exposed to the gas mixture, wherein a direct voltage is applied to the additional electrodes.

10. The device as recited in claim 1, wherein the second electrodes for pumping the gas component are formed by the first electrodes of the amperometric sensor, whose electrode voltage is able to have its polarity reversed for a time interval, before the pressure measuring phase, in such a way that the one of the first electrodes that is shielded by the diffusion barrier is operated as an anode.

11. The device as recited in claim 1, wherein the gas mixture is the exhaust gas of an internal combustion engine and the gas component is oxygen.

12. The device as recited in claim 11, wherein the device is configured as a sensing element to determine oxygen concentration in exhaust gas of an internal combustion engine, electrodes of the sensing element are used as at least on of the two first electrodes of the amperometric sensor and to pump the gas component.

13. The device as recited in claim 12, wherein the sensing element has a Nernst cell made up of a solid electrolyte and two second electrodes situated thereon, a first one of the second electrodes being situated in a measuring chamber in the solid electrolyte, and a second one of the second electrodes being exposed to a pumped oxygen reference in a reference gas channel developed in the solid electrolyte; and a pump cell made up of a solid electrolyte and two pump electrodes situated thereon, an outer one of the pump electrodes being exposed to the exhaust gas and an inner one of the pump electrodes being situated in the measuring chamber;

wherein, in a connecting channel to the exhaust gas which opens out into the measuring chamber, the diffusion path is developed together with the storage volume, the diffusion barrier is situated between the measuring chamber and the storage volume, and the pump electrodes are used intermittently for pumping oxygen and for measuring the gas pressure.

14. The device as recited in claim 12, wherein the sensing element has a Nernst cell made up of a solid electrolyte and two second electrodes situated thereon, a first one of the second electrodes being a measuring electrode and being situated in a measuring chamber developed in the solid electrolyte and a second one of the second electrodes being a reference electrode and being exposed to a pumped oxygen reference in a reference gas channel developed in the solid electrolyte, and a pump cell made up of a solid electrolyte and two pump electrodes situated thereon, and outer one of the pump electrodes being exposed to the exhaust gas and an inner one of the pump electrodes being situated in the measuring chamber;

wherein the reference gas channel is provided with an opening that is exposed to the exhaust gas, and wherein, in the reference gas channel between the reference electrode and the opening, the diffusion path and the storage volume, arranged upstream thereof, are developed, and wherein the diffusion barrier is situated in the reference gas channel on a side of the reference electrode facing away from the diffusion path, and on the side of the diffusion barrier facing away from the reference electrode the second one of the first electrodes, operated as an anode, is situated, and the outer one of the pump electrodes and the reference electrode are drawn upon to pump oxygen, and the outer one of the pump electrodes and the second one of the first electrodes of the amperometric sensor are drawn upon to measure the gas pressure.

15. A sensing element for determining oxygen concentration in exhaust gas of an internal combustion engine, comprising:
   a Nernst cell made up of a solid electrolyte and two electrodes situated thereon, a first one of the electrodes being a measuring electrode and being situated in a measuring chamber developed in the solid electrolyte, and a second one of the electrodes being a reference electrode and being exposed to a pumped oxygen reference in a reference gas channel developed in the solid electrolyte;
   a pump cell made up of the solid electrolyte and two pump electrodes situated thereon, an outer one of the two pump electrodes being exposed to the exhaust gas and an inner one of the pump electrodes being situated in the measuring chamber; and
   an integrated device for measuring pressure in the exhaust gas, the device configured as the sensing element, electrodes of the sensing element used as at least on of the two first electrodes of the amperometric sensor and to pump the gas component, the device including:
      an amperometric sensor that operates according to a limiting current principle, the sensor including two first electrodes mounted on a solid electrolyte, a direct voltage being applied to the electrodes, wherein one of the first electrodes is shielded by a diffusion barrier;
      a measuring element configures to measure the limiting current flowing via the first electrodes as a measure of the gas pressure; and
      an arrangement configured to fix, at least during a pressure measuring phase, a mole fraction of a gas component drawn upon for the pressure measurement upstream of the diffusion barrier to a constant 100%.

16. The sensing element as recited in claim 15, wherein:
   the reference gas channel has an opening that has exhaust gas applied thereto;
   between the reference electrode and the opening, a diffusion path and an oxygen storage volume being arranged in front of the diffusion path in the direction towards the reference electrode;
   on a side of the reference electrode facing away from the diffusion path, an additional electrode, separated by a diffusion barrier, is situated; and
   for measuring the gas pressure, the reference electrode is operated in such a way that a constant mole fraction of the oxygen of 100% is present in the chamber, and the limiting current flowing via the outer pump electrode and the additional electrode is recorded as a measure for the exhaust gas pressure.

17. The sensing element as recited in claim 15, wherein:
   the reference gas channel has an opening that has exhaust gas applied thereto;
   between the reference electrode and the opening a diffusion path and an oxygen storage volume, being arranged in front of it in a direction towards the reference electrode, and being separated from the reference electrode by a diffusion barrier; and
   at intervals, such a voltage is applied to the outer pump electrode and the reference electrode that a constant mole fraction of the oxygen of 100% is present in the oxygen storage volume, and after switching over the voltage, the limiting current flowing via the outer pump electrode and the reference electrode is recorded as a measure for the pressure of the exhaust gas.

18. The sensing element as recited in claim 10, wherein:
   a diffusion path and an oxygen storage volume arranged in front of the diffusion path in the direction towards the measuring chamber, are developed in a connecting channel to the exhaust gas, that opens out into the measuring chamber;
   the oxygen storage volume being separated from the measuring chamber by the diffusion barrier; and
   the pump cell is operated at intervals in such a way that a constant mole fraction of oxygen of 100% is present in the oxygen storage volume, and after switching over a direction of the current in the pump cell, the limiting current flowing via the pump electrodes is recorded as a measure for the pressure of the exhaust gas.

19. The sensing element as recited in claim 16, wherein the diffusion barrier has a porosity required for Knudsen diffusion and the diffusion path has a pressure gradient that is as small as possible.

20. The sensing element as recited in claim 11, wherein the oxygen storage volume is formed by a chamber and the diffusion path is formed by at least one additional diffusion barrier made of ceramic material.

* * * * *